US008883077B2

(12) United States Patent
Worley et al.

(10) Patent No.: US 8,883,077 B2
(45) Date of Patent: Nov. 11, 2014

(54) DISINFECTING, NONBLEACHING N-HALAMINE FOR USE WITH CONTACT LENS

(75) Inventors: Shelby D. Worley, Auburn, AL (US); Xuehong Ren, Bothell, WA (US); Hasan B. Kocer, Auburn, AL (US)

(73) Assignee: Auburn University, Auburn, AL (US)

( * ) Notice: Subject to any disclaimer, the term of this patent is extended or adjusted under 35 U.S.C. 154(b) by 577 days.

(21) Appl. No.: 13/029,906

(22) Filed: Feb. 17, 2011

(65) Prior Publication Data

US 2011/0200484 A1    Aug. 18, 2011

Related U.S. Application Data

(60) Provisional application No. 61/305,747, filed on Feb. 18, 2010.

(51) Int. Cl.
| | | |
|---|---|---|
| *A61L 2/18* | (2006.01) | |
| *A61K 31/415* | (2006.01) | |
| *A01N 43/50* | (2006.01) | |
| *A01N 59/00* | (2006.01) | |

(52) U.S. Cl.
CPC ............... *A01N 43/50* (2013.01); *A01N 59/00* (2013.01)
USPC ............................................ 422/37; 514/386

(58) Field of Classification Search
USPC ............................................ 422/37; 514/386
See application file for complete search history.

(56) References Cited

U.S. PATENT DOCUMENTS

| 5,057,612 A | 10/1991 | Worley et al. |
|---|---|---|
| 2007/0155852 A1* | 7/2007 | Rathore ........................ 523/106 |
| 2010/0303930 A1 | 12/2010 | Carey et al. |

OTHER PUBLICATIONS

Kenawy et al., "The Chemistry and Applications of Antimicrobial Polymers: A State of the Art Review", Bio Macromolecules, May 1, 2007, vol. 8, No. 5, American Chemical Society, pp. 1359-1384.
Tsao et al., "Novel N-Halamine Disinfectant Compounds" Biotechnol.Prog., Jan. 1, 1991,vol. 7, No. 1, pp. 60-66.
Worley et al., "Halamine Water Disinfectants, CRC Critical Reviews in Environmental Control", Jan. 1, 1988, vol. 18, Issue 2, pp. 133-175.
Worley et al., "Biocidal Polymers", Trends Poli Sci., pp. 364-370, vol. 4, No. 11, Nov. 1, 1986.
Worley et al., Use of N-chloro-4-hydroxy-2,2,6,6-tetramethylpiperidine (TMP-CI) in Aqueous.

* cited by examiner

*Primary Examiner* — Kevin Joyner
(74) *Attorney, Agent, or Firm* — Haverstock & Owens LLP

(57) ABSTRACT

A disinfecting, nonbleaching N-halamine for use in contact lens soaking solutions. The N-halamine compound is soluble in water and contact lens formulation solutions to the extent necessary to provide disinfection, but not to cause significant bleaching of dye materials incorporated into the contact lenses.

4 Claims, 2 Drawing Sheets

DISINFECTING, NONBLEACHING N-HALAMINE FOR USE WITH CONTACT LENS

CROSS REFERENCE TO RELATED APPLICATIONS

This application claims priority to U.S. Provisional Application Ser. No. 61/305,747, filed on Feb. 18, 2010, hereby incorporated by reference in its entirety for all of its teachings.

TECHNICAL FIELD OF THE INVENTION

The present invention relates to the use of a very stable, minimally oxidizing N-halamine compound which is able to be employed for disinfecting contact lenses in a soaking formulation, while causing minimal bleaching of dyes incorporated into the contact lenses over several months periods of exposure to same.

BACKGROUND

For three decades research and development work in the laboratories of Worley and co-workers has proceeded with the goal of producing novel antimicrobial compounds (for example, see review articles Worley, S. D., Williams, D. E., "Halamine Water Disinfectants", CRC Crit. Rev. Environm. Cntrl. 1988, 18, 133; Worley, S. D., Sun, G., "Biocidal Polymers", Trends Polym. Sci. 1996, 4, 364; Kenawy, E., Worley, S. D., Broughton, R. M., "The Chemistry and Applications of Antimicrobial Polymers, A State of the Art Review", Biomacromolecules 2007, 8, 1359, and the references incorporated therein). All of the work has focused upon a class of compounds known as organic N-halamines which are generally heterocyclic monomers or polymers containing nitrogen-halogen bonds. The most stable of these compounds with regard to the release of bleaching free halogen in aqueous solution are those containing N—Cl covalent bonds stabilized by electron-donating substituents, e.g. alkyl groups such as methyl groups, attached to the carbon atoms in the cyclic structures directly linked to the nitrogen atom containing the chlorine atom. The mechanism by which these N-halamine compounds inactivate pathogenic microorganisms is through a direct contact in which the N-halamine donates its halogen atom to the biological cell, wherein the cell is inactivated through an oxidation process. If the N—Cl bond on the N-chloramine is sufficiently strong, the disinfection process will be slower than for "free chlorine", the antibacterial agent which is present in household bleach. However, if free chlorine is not appreciably released from an N-chloramine into aqueous media, then undesirable chemical processes such as corrosion and bleaching will be minimized.

There is a need for soaking formulations which can be used to maintain disinfection of contact lenses so as to prevent eye infections in the wearer. Any cyclic N-chloramine will be useful in this regard, particularly if it is supplemented by an oxidant such as sodium chlorite so as to accentuate the inactivation process kinetics. For example, the N-halamine, 1-chloro-2,2,6,6-tetramethyl-4-piperidinol, has been demonstrated to inactivate pathogens which are important in ophthalmic uses (see Carey, et al., US 2010/0303930 A1 and Worley, et al., Provisional application Nos. 61/065,320 filed on Feb. 11, 2008, 61/153,665, filed on Feb. 19, 2009, and 61/305,747 filed on Feb. 18, 2010). However, this compound at concentrations necessary for adequate disinfection releases sufficient free chlorine into contact lens soaking formulations to bleach out the dyes incorporated into the contact lenses which are necessary for tinting and ultraviolet protection, rendering the compound of little use for contact lens applications.

SUMMARY OF THE INVENTION

The present invention relates to the use of the N-chloramine compound 1-chloro-2,2,5,5-tetramethyl-4-imidazolidinone, which is an exceptionally stable N-chloramine toward hydrolysis in aqueous solution, in contact lens soaking formulations for the purpose of inactivating pathogenic microorganisms, while not causing significant bleaching of the dyes incorporated into the contact lenses.

DETAILED DESCRIPTION

Figure 1:
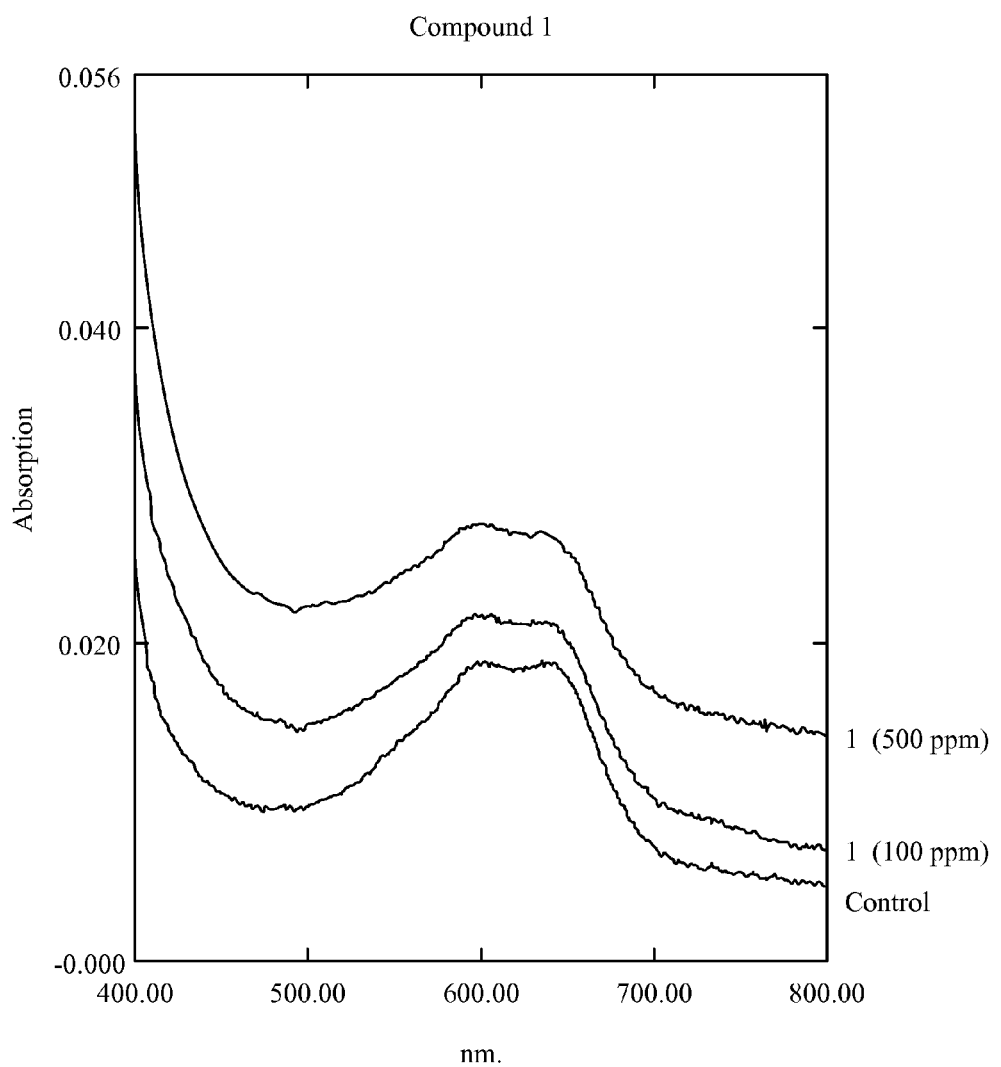
FIG. 1 illustrates a UV/VIS spectra of contact lenses treated with Unisol 4 formulation including compound 1 daily over a 2-month period, wherein the control contained no N-halamine disinfectant.

Two antimicrobial N-chloramine compounds which are soluble in aqueous media and which would be considered to be candidates for disinfection of contact lenses in a soaking formulation application, whose structures are shown below, are 1-chloro-2,2,5,5-tetramethyl-4-imidazolidinone (henceforth referred to as compound 1) and 1-chloro-2,2,6,6-tetramethyl-4-piperidinol (henceforth referred to as compound 2).

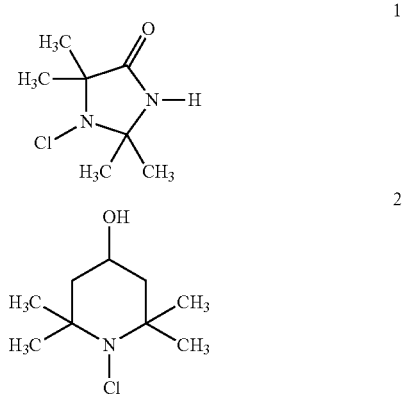

Upon inspection of the chemical structures, one might expect that the two compounds should act similarly in their efficacies as antimicrobials and in their bleaching reactions in contact lens soaks, since both are cyclic hindered amine derivatives with four stabilizing inductively electron-donating methyl groups on the carbon atoms surrounding the nitrogen atom to which the oxidizing chlorine atom is bonded. Both compounds are indeed antimicrobial when dissolved in aqueous media, such as contact lens soaking formulations. However, in this application it will be shown that unexpectedly compound 1 is quite un-reactive in a bleaching reaction with the dyes in contact lenses, whereas compound 2 is very reactive in this undesirable process.

Both of the N-chloramine compounds mentioned above are able to easily be synthesized using methods known to those of skill in the art. Aqueous solutions of the un-halogenated amine precursor for either compound may be simply exposed to a dilute aqueous solution of household bleach (e.g., sodium hypochlorite) or sodium chlorite or by bubbling in chlorine gas to form the N-chloramine. For example, compound 1 has been prepared by Worley, et al., by using chlorine gas to react with an aqueous alkaline solution of the precursor amine (see Tsao, et al., "Novel N-Halamine Disinfectant Compounds", Biotechnol. Prog. 1991, 7, 60 or Worley, et al., U.S. Pat. No. 5,057,612). It can also be purchased commercially from the HaloSource Corporation in Bothell, Wash. The precursor 2,2,5,5-tetramethyl-4-imidazolidinone is able to be prepared according to the method outlined in Tsao, et al., "Novel N-Halamine Disinfectant Compounds", Biotechnol. Prog. 1991, 7, 60 or Worley, et al., U.S. Pat. No. 5,057,612. Compound 2 is able to be prepared by reaction of commercial (Aldrich Chemical Company, Milwaukee, Wis.) 2,2,6,6-tetramethyl-4-piperidinol with dilute household bleach. The oxidative chlorine contents, and hence purities, of both compounds are able to be measured using a standard iodometric/thiosulfate titration procedure. Pure compounds 1 and 2 contain 20.1 and 18.5 percent by weight oxidative chlorine, respectively. Their solubilities in water at 22° C. are 1930 and 6815 mg/L, respectively. The weight percents of oxidative chlorine present under these saturated conditions at 22° C. for the two compounds are 388 and 1260 mg/L, respectively. Both compounds are adequately soluble for a contact lens soaking application in which about 10 to 1000 mg/L, preferably about 60 mg/L, would be required to provide adequate disinfection efficacy.

Disposable soft contact lenses, such as those manufactured by Johnson & Johnson Vision Care, Inc. (ACUVUE 2), which contain a blue dye for ultraviolet light protection, are recommended by the manufacturer to be worn for no more than 14 days (or 6 days and nights of continued wear). Thus, it is necessary for an active antimicrobial in a soak to be an effective disinfectant and to cause no appreciable bleaching of the dye in the lens over that period of time. Furthermore, it is necessary that the active antimicrobial be compatible with other components in the contact lens soaking formulation such as buffering agents, preservatives, surfactants, water-soluble polymers, antioxidants, stabilizing agents, co-solvents, tonicity agents, pH adjustment agents (target pH 6.0-8.0), and other disinfectants. For example, a contact lens soaking formulation (Unisol 4) manufactured by Alcon Laboratories, Inc. is an aqueous solution containing sodium chloride, boric acid and sodium borate, as stated by the manufacturer. The user is directed to discard the solution once opened after 30 days to maintain sterility. Certain chlorite salts, such as sodium chlorite, have been shown to enhance the antimicrobial property of N-halamines (see Carey, et al., US 2010/0303930 A1), although these could also contribute to the undesirable bleaching process for the dyes in the contact lenses.

Compound 1 is able to easily be combined with current manufactured contact lens soaking formulations such as Unisol 4 (Alcon Laboratories, Inc.) and packaged in solution form, or it is able to be produced as a powder or tablet and added to a water-based formulation as needed; the tablet is able to contain other constituents such as fillers and binders. Although the primary use of compound 1 envisioned in this application is as a non-bleaching antimicrobial for a contact lens soaking formulation, it is conceivable that the compound may also be useful in other ophthalmic applications such as in eye drops for the treatment of infections. Likewise, it is conceivable that the compound could be used in aqueous formulations for the treatment of ear and sinus infections.

The present invention is more particularly described in the following examples which are intended as illustrative only since numerous modifications and variations therein will be apparent to those skilled in the art.

EXAMPLES

Example 1

Disinfection Efficacy of Compound 1

The antimicrobial efficacy of compound 1 was evaluated against the pathogen *Staphylococcus aureus* (ATCC 25923) in aqueous solution at 22° C. and pH values of 4.5, 7.0, and 9.5. Solutions containing about $1 \times 10^6$ colony forming units (CFU) per mL final cell densities of bacteria were prepared and treated with compound 1 at a concentration of 5 mg/L total chlorine concentration (25 mg/L compound concentration). Aliquots were removed at predetermined contact times and quenched with sterile 0.02 N sodium thiosulfate to terminate disinfection action. Then serial dilutions were made into sterile saline solution, and 25 µL aliquots of each dilution were applied to the dried surface of a Petri dish containing tryptic soy agar. After 48 hours of incubation at 37° C., colony counts for each dilution were made. The results of three replicates were averaged. Control samples containing no disinfectant were handled in the same manner. Inactivation of the pathogen was considered to be at least 99.9999% (6 logs) when no viable colonies were detected in the thiosulfate-quenched aliquots. The control samples showed no measureable disinfection.

The results of the experiment showed that: for pH 4.5, 96% inactivation occurred after 10 minutes contact, and 60 minutes were required for 99.9999% inactivation; for pH 7.0, 4.4% inactivation occurred after 10 minutes contact time, and 588 minutes were required for 99.9999% inactivation; for pH 9.5, 50% inactivation occurred after 10 minutes contact time, and 454 minutes were required for 99.9999% inactivation. Obviously lesser inactivations at pH 7.0, e.g. 4 logs, would have been obtained in a contact time of less than 588 minutes.

These results show that compound 1 is antimicrobial even at a very low concentration (5 mg/L total chlorine). At a higher concentration, e.g. the recommended use concentration of about 60 mg/L compound (about 12 mg/L total chlorine concentration) the disinfection efficacy is increased.

Example 2

Stability of Compound 1 in Aqueous Media

The stabilities of compound 1 in aqueous solution and in a contact lens soak formulation (Unisol 4 manufactured by Alcon Laboratories, Inc.) were determined at 22° C. by using the standard iodometric/thiosulfate titration procedure. In water buffered to pH 7.0 at 22° C., the compound at a starting concentration of 10 mg/L total chlorine lost less than 5% of its oxidative chlorine over a storage period of 50 days. In about 4 mL of Unisol 4 at a starting concentration of about 20 mg/L total chlorine in the presence of an ACUVUE 2 contact lens (manufactured by Johnson & Johnson Vision Care, Inc.) in a lens holder manufactured by Alcon Laboratories, Inc., the loss of oxidative chlorine over 60 days was about 21%. In contrast, in an analogous experiment with compound 2 in the Unisol 4, the loss was about 54% over just 30 days. These data indicate that compound 1 is much more stable than is compound 2 in contact lens soak formulations.

Example 3

A Comparison of the Bleaching Reaction for Contact Lens Dyes for Compounds 1 and 2

An ACUVUE 2 contact lens manufactured by Johnson & Johnson Vision Care, Inc., which contained a blue dye, was placed in a contact lens holder manufactured by Alcon Laboratories, Inc. To the lens holder containing the contact lens was added a 4 mL portion of Unisol 4 manufactured by Alcon Laboratories, Inc. which contained: no disinfectant additive (a control), or compound 1 at either a 100 mg/L or a 500 mg/L concentration, or compound 2 at either a 100 mg/L or a 500 mg/L concentration. The contact lenses were observed visually over a period of days. The blue color did not appear to change in the contact lenses exposed to the control solution or to the solutions containing compound 1 even after storage for 2 months. In contrast, the blue color disappeared completely for the contact lens stored in 500 mg/L of compound 2 within a week and for that stored in 100 mg/L of compound 2 within 2 weeks.

In order to obtain a more accurate assessment of the bleaching reaction, at the end of the study each contact lens was placed into a quartz cuvette for spectrophotometric analysis (Shimadzu UV-2450 UV/VIS Spectrophotometer, Shimadzu Scientific Instruments, Inc., Columbia, Md.). In one study the Unisol 4 containing compound 1 was changed daily in the contact lens holder. FIG. 1 shows the UV/VIS spectra of the contact lenses soaked in compound 1 at the two different concentrations (500 parts per million (ppm) and 100 ppm) over a period of 2 months versus the control contact lens. Specifically, FIG. 1 illustrates UV/VIS spectra of contact lenses treated with Unisol 4 formulation, including compound 1, daily over a 2-month period, wherein the control contained no N-halamine disinfectant. The control and compound 1 were both refreshed daily over the 2-month period. From the absorption bands centered near 600 nm, it is evident that little bleaching occurred over the 2 month period of storage for compound 1.

Figure 2:
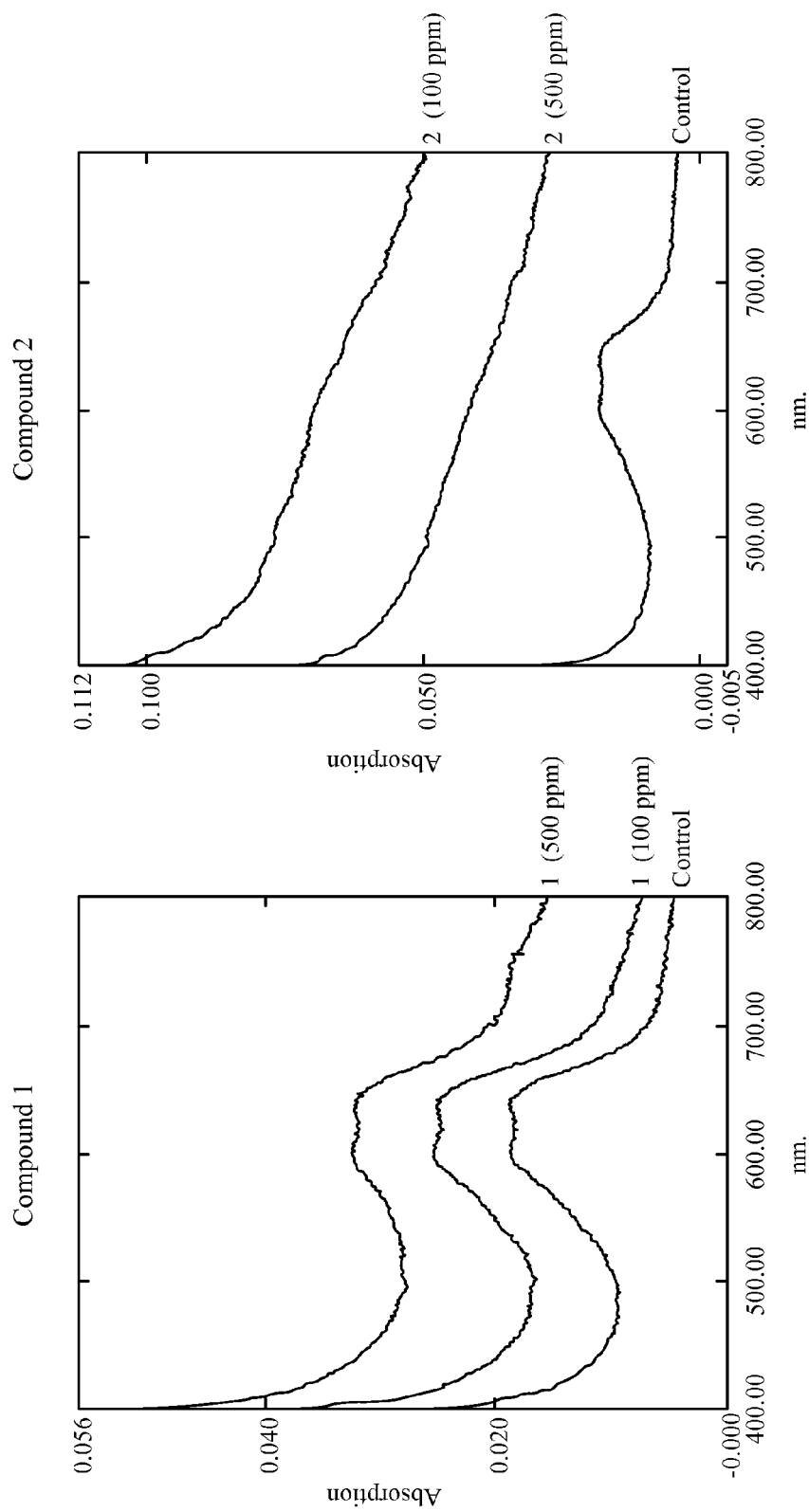
FIG. 2 illustrates a UV/VIS spectra of contact lenses treated with Unisol 4 formulation including compound 1 over a 2-month period and compound 2 over a 1-month period, wherein the control contained no N-halamine disinfectant.

Also, compounds 1 and 2 were directly compared as to their bleaching tendencies of the blue dye in the contact lenses as shown in FIG. 2. Specifically, FIG. 2 illustrates UV/VIS spectra of contact lenses treated with Unisol 4 formulation including compound 1 over a 2-month period and a Unisol 4 formulation including compound 2 over a 1-month period, wherein the control contained no N-halamine disinfectant. In this case, the solutions (including compound 1 shown in the graph on the left, compound 2 shown in the graph on the right, and the control shown in both graphs) were not refreshed during the storage period. It is obvious from the spectra in FIG. 2 that compound 1 is far superior to compound 2 in its resistance to causing undesirable bleaching of the contact lenses, especially since the data for compound 1 are for 2 months of storage, while the data for compound 2 are for only 1 month of storage.

Throughout this application, various publications are referenced. The disclosures of these publications in their entireties are hereby incorporated by reference in this application in order to more fully describe the compounds, compositions, and methods described herein.

Various modifications and variations are able to be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed is:

1. A method of disinfecting and cleaning a contact lens comprising contacting the contact lens with a sterile, aqueous composition comprising N-chloramine compound 1-chloro-2,2,5,5-tetramethyl-4-imidazolidinone having the structure

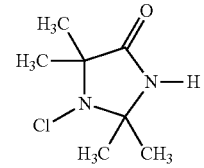

in an ophthalmic formulation so as to provide an antimicrobial function, wherein the method produces a change in absorption value of no greater than 0.01 as measured by a spectrophotometer at a wavelength of 620 nanometers after a contact lens with any dye contained within the contact lens is stored in said composition for two months.

2. A method according to claim 1 wherein said composition has a pH of 6.0 to 8.0.

3. A method according to claim 2 wherein said composition has a pH of 6.5 to 7.8.

4. A method of disinfecting ophthalmic surfaces comprising temporarily soaking said surfaces with a sterile aqueous composition comprising N-chloramine compound 1-chloro-2,2,5,5-tetramethyl-4-imidazolidinone having the structure

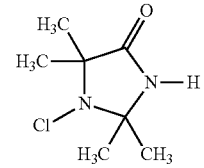

in an ophthalmic formulation so as to provide an antimicrobial function, wherein the method produces a change in absorption value of no greater than 0.01 as measured by a spectrophotometer at a wavelength of 620 nanometers after an ophthalmic surface with any dye contained within the ophthalmic surface is stored in said composition for two months.

* * * * *